United States Patent [19]
Grass et al.

[11] Patent Number: 6,156,731
[45] Date of Patent: *Dec. 5, 2000

[54] POLYPEPTIDE COMPOSITION FOR ORAL ADMINISTRATION

[75] Inventors: George M. Grass, Mountain View, Calif.; Stephanie A. Sweetana, Indianapolis, Ind.

[73] Assignee: G. D. Searle & Co., Skokie, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 08/567,501

[22] Filed: Dec. 5, 1995

Related U.S. Application Data

[63] Continuation of application No. 07/350,067, May 10, 1989, abandoned.

[51] Int. Cl.[7] .......................... A61K 38/00; A61K 39/00; C07K 5/00; C07K 7/00
[52] U.S. Cl. ................... 514/15; 514/2; 514/14; 514/13; 514/16; 514/12; 530/300; 530/311; 530/313; 530/324; 530/326; 530/327; 530/328; 424/464; 424/185.1
[58] Field of Search .............................. 514/2, 3, 12, 13, 514/14, 15, 16; 530/300, 311, 313, 324, 326, 327, 328; 424/464, 185.1

[56] References Cited

U.S. PATENT DOCUMENTS

| | | |
|---|---|---|
| 4,234,571 | 11/1980 | Nestor et al. . |
| 4,291,022 | 9/1981 | Sadrin et al. . |
| 4,310,518 | 1/1982 | Freidinger . |
| 4,342,671 | 8/1982 | Sarantakis . |
| 4,579,730 | 4/1986 | Kidron et al. ............................. 424/19 |
| 4,582,820 | 4/1986 | Teng ............................................ 514/3 |
| 4,728,638 | 3/1988 | Bauer et al. . |
| 4,801,577 | 1/1989 | Nestor et al. . |
| 4,994,439 | 2/1991 | Longenecker et al. ..................... 514/3 |

FOREIGN PATENT DOCUMENTS 0111841   12/1983   European Pat. Off. .

OTHER PUBLICATIONS

M.J. Humphrey and P.S. Ringrose, Drug Metab. Reviews, 17: 283–310, (1986).
M.L. Gardner and D. Wood, Biochem. Soc. Trans., 17: 934–937 (1989).
V.V. Mozhaev, I.V. Berezin, K. Martinek, CRC Crit. Rev. Biochem., 23: 235–281 (1988).
H.P. Merkle, Eur. J. Pharm. Sci., 2: 19–21 (1994).
J.A. Fix, J. Pharm. Sci., 85: 1282–1285 (1996).
M. Kidron, H. Bar–On, E.M. Berry, and E. Ziv, Life Sciences, 31: 2837–2841 (1982).
V.H. Lee, Crit. Rev. Ther. Drug Carrier Systems, 5: 69–97 (1988).
O. Siddiqui and Y.W. Chien, Crit. Rev. Ther. Drug Carrier Systems, 3: 195–208 (1987).
M. Saffran et al., Science, 233, 1281 (1986).
M.V. Nekola et al, Science 218, 160 (1982).
N. Yokoo et al., Yakugaku Sasshi, 108(2), 164–169 (1988).
S. Fujii et al., J. Pharm. Pharmacol., 37, 545–549 (1984).
E. Ziv et al., Life Sciences, 29(8), 803–809 (1981).
E. Ziv et al., Biochem. Pharmacol., 36(7), 1035–1039 (1987).
R. Z. Kai et al., Proc. Natl. Acad. Sci. USA, 83, 1896 (1986).
W. Bauer et al., Life Sciences, 31, 1133 (1982).
T. Karashima et al., Life Sciences, 41, 1011 (1987).
T.W. Redding et al., Proc. Natl. Acad. Sci., 80, 1078 (1983).
J.P. Moreau et al., Life Sciences, 40, 419 (1987).

*Primary Examiner*—Avis M. Davenport
*Attorney, Agent, or Firm*—Fitzpatrick, Cella, Harper & Scinto

[57] ABSTRACT

There is disclosed a composition containing a biologically active polypeptide selected from LHRH, an LHRH analog, somatostatin and a somatostatin analog, in a therapeutically effective amount, a membrane permeability enhancing agent, and a protease enzyme inhibitor enveloped within an enteric coating. The composition possesses enhanced bioavailability upon oral administration.

16 Claims, 4 Drawing Sheets

FIGURE 1

PLASMA CONCENTRATION OF NAFARELIN AFTER ORAL DOSE OF FORMULATION A IN RHESUS MONKEY

FIGURE 3
PLASMA CONCENTRATION OF NAFARELIN AFTER ORAL DOSE OF FORMULATION C IN RHESUS MONKEY

FIGURE 4
PHARMACOKINETIC SIMULATION OF NAFARELIN
IN RHESUS MONKEY AND HUMAN

POLYPEPTIDE COMPOSITION FOR ORAL ADMINISTRATION

This application is a continuation of application Ser. No. 07/350,067, filed May 10, 1989, abandoned.

BACKGROUND OF THE INVENTION

1. Field of the Invention

The present invention relates to a pharmaceutical composition containing a biologically active polypeptide suitable for oral administration. More particularly, the present invention relates to a pharmaceutical composition for oral administration containing one of LHRH, an LHRH analog, somatostatin and a somatostatin analog. In another aspect, the present invention relates to a process for rendering the biologically active polypeptide suitable for oral administration.

2. Description of Related References

M. Kidron et al., U.S. Pat. No. 4,579,730 (Apr. 1, 1986), disclose a pharmaceutical composition for the oral administration of insulin comprising insulin, a bile acid or alkali metal salt thereof to promote absorption of insulin, a protease inhibitor to protect insulin against proteolysis, and the use of enterocoating of the above active mixture.

M. Saffran et al., Science, Vol. 233, 1281 (1986), describe that the oral administration of polypeptide drugs has been well known to be precluded by their digestion in the stomach and small intestine. These authors further describe that peptide drugs can be protected against attack by digestive enzymes by coating the drug with an impermeable polymer film wherein the coating polymer is not susceptible to the action of digestive enzymes. The ability of microflora to reductively cleave azoaromatic bonds has been known. Thus, azoaromatic polymer coated capsules and pellets of vasopressin or insulin were used to determine whether the azoaromatic polymer could be used for the oral delivery of peptide drugs. Vasopressin and insulin were found to be absorbed after administration of the capsules by depositing the capsules in the stomach of rats. Further, oral administration to rats of vasopressin and insulin protected with azoaromatic polymer coatings produced biological responses characteristic of the peptide hormones. These results were taken to show that the azoaromatic polymer delivery system operates in principle.

E. German Patent Application No. DD 252 539 A published Dec. 23, 1987, Derwent Abstract 88-133631/20, discloses oral administration of active peptides such as insulin, Substance P, GnRH or its analogs, atrial natriuretic peptide, a synthetic thymus peptide, an ACE- or renin-inhibiting peptide or a neuropeptide in the form of controlled-release compositions comprising the active peptide immobilized on a carrier, a gastrointestinal absorption promoter, and a protease inhibitor. The absorption promoter is a protein/fatty acid condensate and the protease inhibitor is epsilon-aminocaproic acid or derivative thereof or aprotinin.

European Patent Application No. EP 177,342 A published Sep. 4, 1986, Derwent Abstract 86-095678/15, discloses oral therapeutic protein formulations with enhanced absorption comprising as active ingredient an amphilipophilic protein of molecular weight over 12,000, a lipophilic water-immiscible compatible vehicle usable in enteric formulations, and a gastrointestinal tract absorption enhancing agent. Described as particularly suitable for administration as active ingredient are human growth hormone, human alpha- or gamma-interferon, human tissue plasminogen activator, human tumor necrosis factor, bovine growth hormone or alpha- or gamma-interferon, porcine growth hormone, chicken growth hormone, or structurally similar bioactive equivalents of the above. Mineral oil is mentioned as the preferred lipophilic vehicle. There is mentioned as the gastrointestinal tract absorption enhancing agent hydoxyaryl or hydroxylalkylaryl acids and their salts, esters or amides, or enamine derivatives of 1,3-dicarbonyl compounds and aminoacids and their salts, amides or esters. Suitable vehicles include triglycerides, esterified glycols, polyglycols with hydrophobic alkyl side chains, phospholipids, sterols and especially mineral oil. As the absorption enhancer, there is mentioned that an agent having Ca chelating properties may also be present. A preferred absorption enhancer is sodium salicylate.

European Patent Application No. EP 111,841 A published Jun. 27, 1984, Derwent Abstract 84-159888/26, discloses nasal compositions comprising a nona- or deca-peptide or its salts having LHRH agonist or antagonist activity together with a bile acid or its salt as a surfactant in aqueous solution, the composition having greatly enhanced absorption across the nasal membrane. Representative of the LHRH analog is the compound represented by the formula (pyro)Glu-His-Trp-Ser-Tyr-3-(2-naphthyl)-D-Ala-Leu-Arg-Pro-Gly-NH$_2$.

Sodium glycocholate was used as the surfactant, together with buffer.

M. V. Nekola et al., Science, Vol. 218, 160 (1982) disclose suppression of ovulation in the rat by an orally active antagonist of luteinizing hormone-releasing hormone. The active compound was given by gavage on the afternoon of proestrus and ovulation was delayed for at least one day in all animals given 2 mg of antagonist and oral administration of the same also blocked preovulatory surge of luteinizing hormone.

H. Okada et al., J. Pharm. Sci., 71(12), 1367 (1982), evaluate the absorption of a potent luteinizing hormone-releasing hormone analog, leuprolide, through different routes such as, for example, vaginal, rectal, nasal, and oral administration, in rats. For oral administration, a mixed micellar solution with monoolein, sodium taurocholate, and sodium glycocholate was prepared. Vaginal administration showed the greatest potency among nonparenteral routes followed successively by rectal, nasal and oral administration.

N. Yokoo et al., Yakugaku Zasshi, 108. (2), 164–169 (1988) and S. Fujii et al., J. Pharm. Pharmacol., 37, 545–549 (1984), disclose the use of the chymotrypsin inhibitor, 4-(4-isopropylpiperazinocarbonyl)phenyl 1,2,3,4-tetrahydro-1-naphthoate methanesulfonate (FK-448) in the promoting effect on the intestinal absorption of insulin based on the inhibition of proteolytic enzymes.

E. Ziv et al., Life Sciences, 29 (8), 803–809 (1981) and E. Ziv et al., Biochemical Pharmacology, 36 (7), 1035–1039 (1987), disclose the absorption of insulin mixed with sodium deoxycholate or sodium cholate from the rectal mucosa of diabetic and non-diabetic rats.

Biologically active, that is, hormonally active, polypeptides comprise a diverse group of polypeptides. Because of their functional specificity, they can be conveniently grouped into discrete classifications on the basis of physiological effect. For example, LHRH and analogs thereof act on the anterior pituitary gland to effect release of hormones which affect the activity of reproductive organs. Somatostatin analogs block secretion of growth hormone from the pituitary gland, secretion of gastric acid and pepsin from the stomach lining, and release of both glucagon and insulin from the pancreatic islets. Somatostatin also acts to inhibit the absorption of glucose, amino acids and fat from the gastrointestinal (GI) tract as well as to inhibit GI motility.

LHRH analogs and somatostatin analogs are relatively short acting in the body. Thus, attempts have been made to modify the compounds to obtain compounds that are longer acting and more potent.

LHRH analogs include compounds having agonist or antagonist effects. Representative, known LHRH agonists include those compounds that are disclosed in Nestor et al., U.S. Pat. No. 4,234,571 (Nov. 18, 1980). Representative, known LHRH antagonists include those compounds disclosed in Nestor et al., U.S. Pat. No. 4,801,577 (Jan. 31, 1989).

Other representative LHRH analogs include those nona- or decapeptides having LHRH agonist or antagonist activity disclosed, along with processes for preparation thereof, in the following U.S. Pat. Nos. 3,813,382; 3,843,065; 3,849,389; 3,855,199; 3,886,135; 3,890,437; 3,892,723; 3,896,104; 3,901,872; 3,914,412; 3,915,947; 3,929,759; 3,937,695; 3,953,416; 3,974,135; 4,010,125; 4,018,914; 4,022,759; 4,022,760; 4,022,761; 4,024,248; 4,034,082; 4,072,668; 4,075,189; 4,075,192; 4,086,219; 4,101,538; 4,124,577; 4,124,578, 4,143,133; 4,234,571; 4,253,997; 4,292,313; 4,341,767.

Representative, known somatostatin analogs include those described in the following references: U.S. Pat. Nos. 4,728,638; 4,342,671; 4,310,518; and 4,291,022; European Patents No. 0,022,578 and 0,175,644; *Proc. Natl. Acad. Sci. USA,* 83, 1896(1986); *Life Sciences.* 31, 1133(1982); *Life Sciences,* 41, 1011(1987); *Proc. Natl. Acad. Sci. USA.* 80, 1078(1983); and *Life Sciences.* 40, 419(1987).

SUMMARY OF THE INVENTION

This invention is a polypeptide composition for oral administration comprising a biologically active polypeptide selected from LHRH, an LHRH analog, somatostatin and a somatostatin analog, in a therapeutically effective amount, a membrane permeability enhancing agent, and a protease enzyme inhibitor enveloped within an enteric coating material. The composition possesses enhanced bioavailability upon oral administration when compared with oral administration of heretofore known compositions of said biologically active polypeptides.

In another aspect, this invention is a process for providing a pharmaceutical composition suitable for oral administration comprising: providing a therapeutically effective amount of a biologically active polypeptide, admixing therewith a membrane permeability enhancing agent selected from a bile acid or an alkali metal salt thereof and a non-toxic amount of a protease inhibitor, and an enteric coating material, and providing said mixture in a pharmaceutically acceptable dosage form selected from capsule and tablet forms.

DESCRIPTION OF THE FIGURES

FIGS. 1 and 2 are set forth for comparison purposes.

TABLE I sets out Formulations A, B, and C and the composition of the enteric coating medium.

DETAILED DESCRIPTION OF THE INVENTION

Administration of the biologically active polypeptide therapeutic agent useful in the composition according to this invention by means of other modes of administration, particularly by injection, is known. However, the daily or even more frequent injection of such a therapeutic (or prophylactic) agent is inconvenient and often painful. Additionally, severe side effects at the site of injection may occur.

Polypeptide therapeutic agents generally cannot be administered orally because they are susceptable to enzymatic attack and degradation in the presence of enzymes commonly and prevalently found in the upper gastrointestinal tract, that is in the mouth and stomach. The present invention overcomes the problems described above.

Although Kidron, et al. U.S. Pat. No. 4,579,730, mentioned above, describe an oral insulin composition containing, in addition to insulin (a polypeptide), an absorption enhancing agent and a protease inhibitor and an enterocoating material, the insulin polypeptide molecule has vastly differing chemical and physical characteristics when compared with the therapeutically active polypeptides in the composition according to this invention.

Insulin has a relatively high molecular weight of about 60,000 daltons and comprises three peptide chains affording the molecule a tertiary structure.

The LHRH analogs and somastostatin analogs of the composition according to this invention are much smaller molecules and are devoid of tertiary structure. They are highly potent molecules, and they are considerably more potent than insulin.

Because of the above differences, if it is surprising that LHRH analogs and somastostatin analogs can be formulated into a composition that is suitable for oral administration.

Accordingly, this invention is a pharmaceutical composition suitable for oral administration to a human patient comprising:

(a) a therapeutically effective amount of a biologically active polypeptide selected from the group consisting of LHRH, an LHRH analog, somotostatin and a somastostatin analog;

(b) a membrane permeability enhancing agent selected from a bile acid or an alkali metal salt thereof;

(c) a non-toxic amount of a protease inhibitor; and (d) an enteric coating material, said enteric coating material enveloping the admixture of components (a), (b) and (c).

More particularly, when said polypeptide useful in this invention is an LHRH analog, it may be selected from LHRH agonists and LHRH antagonists.

For purposes of this invention, the expression "LHRH" refers to "luteinizing hormone-releasing hormone" and the expression "ILHRH analog" is meant to encompass LHRH itself as well as other peptides that are structurally related to LHRH or derived from it and that exhibit biological activity similar to that of LHRH. Generally, these compounds are polypeptides having a molecular weight of no more than about 1500.

Preferred LHRH analogs, useful in this invention include those described in the following U.S. Pat. Nos. 3,813,382; 3,843,065; 3,849,389; 3,855,199; 3,886,135; 3,890,437; 3,892,723; 3,896,104; 3,901,872; 3,914,412; 3,915,947; 3,929,759; 3,937,695; 3,953,416; 3,974,135; 4,010,125; 4,018,914; 4,022,759; 4,022,760; 4,022,761; 4,024,248; 4,034,082; 4,072,668; 4,075,189; 4,075,192; 4,086,219; 4,101,538; 4,124,577; 4,124,578; 4,143,133; 4,234,571; 4,253,997; 4,292,313; 4,341,767. The disclosure of these patents is incorporated herein by reference.

Representative examples of preferred LHRH analogs are products, or experimental products, as follows: nafarelin (as its acetate, RS-94991-298), leuprolide acetate, buserelin acetate, Lutrelin acetate, and histrelin.

For purposes of this invention, the expression "somtostatin analog" is meant to encompass somatostatin itself and polypeptides that are structurally related to somatostatin and that exhibit biological activity similar to that of somatostatin. Generally, these are polypeptides having a molecular weight of no more than about 2000.

Preferred somatostatin analogs include those described in the following references: U.S. Pat. Nos. 4,728,638; 4,342,671; 4,310,518; and 4,291,022; European Patents No. 0,022,578 and 0,175,644; Proc. Natl. Acad. Sci. USA, 83, 1896 (1986); Life Sciences. 31, 1133(1982); Life Sciences, 41, 1011(1987); Proc. Natl. Acad. Sci. USA. 80, 1078(1983); and Life Sciences, 40, 419(1987). The disclosure of these publications is incorporated herein by reference.

For convenience in describing polypeptides useful in this invention, the conventional abbreviations for the various common amino acids are used as generally accepted in the peptide art as recommended by the IUPAC-IUB Commission on Biochemical Nomenclature, Biochem. J. 219:345 (1984). Such abbreviations are incorporated herein by reference.

The following is a list of some of these abbreviations:

| Amino Acid | Three-letter abbreviation |
|---|---|
| Alanine | Ala |
| Arginine | Arg |
| Asparagine | Asn |
| Asparic acid | Asp |
| Cysteine | Cys |
| Glutamine | Gln |
| Glutamic acid | Glu |
| Glycine | Gly |
| Histidine | His |
| Isoleucine | Ile |
| Leucine | Leu |
| Lysine | Lys |
| Methionine | Met |
| Phenylalanine | Phe |
| Proline | Pro |
| Serine | Ser |
| Threosine | Thr |
| Tryptophan | Trp |
| Tyrosine | Tyr |
| Valine | Val |

All peptide sequences mentioned herein are written according to the generally accepted convention whereby the N-terminal amino acid is on the left and the C-terminal amino acid is on the right.

The abbreviations herein represent L-amino acids unless otherwise designated as D- or D,L-. Certain amino acids, both natural or non-natural, are achiral, e.g. glycine.

Non-naturally occurring amino acid are designated as the appropriate amino acid with the substituent in pararenthesis. For example, Lys($R_1$) is lysine with an $R_1$ substituent on the ω-amine Arg($R_1,R_2$) and hARG($R_1,R_2$) are arginine and homoarginine, respectively, with an $R_1$ substituent on the ω-nitrogen and an $R_2$ substituent on the ω'-nitrogen of the guanidino moiety.

Specific abbreviations of non-naturally occurring amino acids will be useful in describing polypeptides useful in this invention. Representative non-naturally occuring amino acids which can be employed include the following:

| Amino acid residue | Abbreviation |
|---|---|
| 3-(2-naphthyl)-alanyl | Nal(2) |
| 3-(p-fluorophenyl)-alanyl | pF-Phe |
| 3-(p-chlorophenyl)-alanyl | pCl-Phe |
| N,N'-guanidino-dimethyl-homoarginyl | Dmh, or hArg(Me)$_2$ |
| N,N'-guanidino-(diethyl)-homoarginyl | Deh, or hArg(Et)$_2$ |
| N,N'-guanidino (diisopropyl)-homoarginyl | Dph, or hArg(Pr)$_2$ |
| N,N'-guanidino-(diisopropyl)-homoarginyl | Dih, or Arg (iPr)$_2$ |
| N,N'-guanidino-(dihexyl)-homoarginyl | Dhh, or hArg(hexyl)$_2$ |
| N,N'-guanidino-(ethano)-homoarginyl | Eha or hArg(CH$_2$)$_2$ |
| N,N'-guanidino-(propano)-homoarginyl | Pha, or hArg(CH$_2$)$_3$ |
| N,N'-guanidino-bis-(2,2,2-trifluoroethyl)-homoarginyl | Bth, or hArg(CH$_2$CF$_3$)$_2$ |
| N-guanidino-(ethyl)-homoarginyl | Meh, or hArg(Et) |
| N-guanidino-(propyl) homoarginyl | Prh, or hArg(Pr) |
| N-guanidino-(isopropyl)-homoarginyl | Iph, or hArg(iPr) |
| N-guanidino-(butyl) homoarginyl | Mbh, or hArg(Bu) |
| N,N'-guanidino-(dicyclohexyl) homoarginyl | Dch, or hArg(cyclohexyl)$_2$ |
| N-guanidino-(heptyl) homoarginyl | Hha, or hArg(heptyl) |
| N-guanidino-(ethyl)-arginyl | Mea, or Arg(Et) |
| N-guanidino-(hexyl, methyl) arginyl | Hmh, or hArg(hexyl, methyl) |
| N-guanidino-(butyl, methyl)-arginyl | Bmh, or hArg(butyl, methyl) |
| N$^ε$ isopropyl-lysine | Ipl, or Lys(iPr) |
| N,N'-guanidino-(diisopropyl)-arginyl | Dia, or Arg(iPr)$_2$ |
| N,N'-guanidino-(dicyclohexyl)-arginyl | Dca, or Arg(cyclohexyl)$_2$ |
| N,N'-guanidino-bis (3,3,3,2,2-pentafluoropropyl)homoarginyl | Bph |
| N,N'-guanidino-(3,3,3,3,3-pentafluoropropyl)homoarginyl | Fph |
| N$^G$-ethyl,N$^{G'}$-(2,2,2-trifluoroethyl)homoarginyl | Efh |
| N,N'-guanidino-(diethyl)arginyl | Dea |
| N,N'-guanidino-bis(2,2,2-trifluoroethyl)-arginyl | Bta |

The non-naturally occuring amino acids described herein are prepared by methods well known to those skilled in the art and may be used in either solution phase or solid phase peptide synthesis procedures. (See, for example, Nestor, et.al., J. Med. Chem., 31, 65 (1988)).

The LHRH agonist compounds of greatest interest, and thus more preferred, herein are those polypeptide compounds that are the subject of U.S. Pat. No. 4,234,571 (Nov. 18, 1980) including their pharmaceutically acceptable salts. The disclosure of this patent is incorporated herein by reference. These polypeptides are nonapeptides and decapeptides represented by the formula:

(pyro)Glu-His-V-Ser-W-X-Y-Arg-Pro-Z    (I)

and the pharmaceutically acceptable salts thereof wherein
V is Trp (tryptophyl), Phe (phenylalanyl), or Nal (3-(1-naphthyl)-L-alanyl)
W is Tyr (tyrosyl), Phe, or 3-(1-pentafluorophenyl)-L-alanyl;
X is a D-amino acid residue wherein R is
(a) a carbocyclic aryl-containing radical selected group consisting of naphthyl, anthryl, fluorenyl, phenanthryl, biphenyl, benzhydryl and phenyl substituted with three or more straight chain lower alkyl groups; or
(b) a saturated carbocyclic radical selected from the group consisting of cyclohexyl substituted with three or more straight chain lower alkyl groups, perhydronapthyl, perhydro-2,2-diphenylmethyl and adamantyl;
Y is leucyl, isoleucyl, nor-leucyl or N-methyl-leucyl; and
Z is glycinamide or —NH—$R^1$ wherein
$R_1$ is lower alkyl, cycloalkyl, fluoro lower alkyl or $R_2$ is hydrogen or lower alkyl.

Most preferred LH-RH agonists are those having formula (I) above wherein X is 3-(2-naphenylalanyl-D-alanyl or 3-(2,4,6-trimethylphenyl)-D-alanyl; Z is glycinamine; V is tryptophyl or phenylalanyl; W is tyrosyl and Y is leucyl or N-methylleucyl.

Especially preferred among the LHRH agonists, and the best mode according to this invention, is a polypeptide represented by the formula:

(pyro)Glu.His.Trp.Ser.Tyr.3-(2-napththyl)-D-Ala.

Leu.Arg.Pro.Gly-$NH_2$ (nafarelin, as its acetate; RS-94991-298).

The LHRH antagonist compounds of greatest interest, and thus, more preferred, herein are those polypeptide compounds that are the subject of U.S. Pat. No. 4,801,577, Jan. 31, 1989. These polypeptides are nonapeptides and decapeptides represented by the formula:

A-B-C-Ser-D-E-F-G-Pro-J    (II)

or a pharmaceutically acceptable salt thereof, wherein:
A is an amino acyl residue selected from the group consisting of either the D- or the L- isomer of: N-Ac-D,L-$\Delta^{3,4}$-prolyl, N-Ac-D,L-prolyl, N-Ac-D,L-phenylalanyl, N-Ac-D,L-p-chlorophenylalanyl, N-Ac-D,L,-p-fluorophenylalanyl, N-Ac-3-(1-naphthyl)-D,L-alanyl, N-Ac-3-(2-naphthyl)-D,L-alanyl, and N-Ac-3-(2,4,6-trimethylphenyl)-D,L-alanyl;

B is an amino acyl residue selected from the group consisting of D-phenylalanyl, D-p-chlorophenylalanyl, D-p-fluorophenylalanyl, D-p-nitrophenylalanyl, 2,2-diphenylglycyl, D-α-methyl-p-chlorophenylalanyl and 3-(2-naphthyl)-D-alanyl;

C is an amino acyl residue selected from the group consisting of D-tryptophanyl, D-phenylalanyl, 3-(3-pyridyl)-D-alanyl, and 3-(2-naphthyl)-D-alanyl;

D is an amino acyl residue selected from the group consisting of L-phenylalanyl, L-tyrosyl, and 3-(3-pyridyl)-alanyl, arginyl, or G;

E is 3-(2-naphthyl)-D-alanyl, 3-(3-pyridyl)-D-alanyl, D-tyrosyl, D-tryptophanyl, D-nicotinyl-lysyl, pyridylacetyl-lysyl, D-Glu(AA) or G;

F is an amino acyl residue selected from the group consisting of L-leucyl, L-norleucyl, L-phenylalanyl, L-tryptophanyl, and 3-(2-naphthyl)-L-alanyl;

G is an amino acyl residue selected from the group consisting of the radicals represented by the following structural formulas:

wherein n is 1 to 5;
$R^1$ is alkyl of 1 to 6 carbon atoms or fluoroalkyl;
$R^2$ is hydrogen or $R^1$; or $R^1$—HN—C=$NR^2$ is a ring represented by the following structural formulas:

wherein m is 1 to 4; A is hydrogen or alkyl of 1 to 6 carbon atoms; and X is halo or A; and -continued wherein R³ is hydrogen, alkyl of 1 to 6 carbon atoms, phenyl or phenyl loweralkyl; and J is D-alaninamide; D-leucinamide; glycinamide; or —NHR⁴ wherein R⁴ is lower alkyl or NHCONH₂.

Still more preferred LHRH antagonists are those wherein A is N-Ac-D-Nal(2) or N-Ac-D-pCl-Phe; B is D-pF-Phe or D-pCl-Phe; C is D-Trp, D-Nal(2) or Pal(3); D is Pal(3), Tyr, Arg, Deh, Mbh, Bth, or Pha; E is D-Trp, D-Tyr, D-Nal(2), D-Pal(3), D-Deh, D-Mbh, D-Pha or D-Bth; F is Leu or Phe; G is Deh, Bth, Mbh, or Pha; and J is D-AlaNH₂ or GlyNH₂.

Most preferred LHRH antagonists are those wherein:

A is N-Ac-D-Nal(2);

B is D-pCl-Phe;

C is D-Trp or D-Pal(3);

D is Tyr, Arg, Deh, Mbh, Bth or Pha;

E is D-Trp, D-Pal(3), D-Nal(2), D-Tyr, D-Deh, -Mbh, D-Bth or D-Pha;

F is Leu;

G is Deh, Mbh, Bth or Pha; and

J is D-AlaNH₂.

Especially preferred among said LHRH antagonist are polypeptides represented by the formula:

A-B-C-Ser-D-E-F-G-Pro-J    (II)

wherein A in N-Ac-D-Nal(2), B is D-pCl-Phe, C is D-Pal(3), D is Tyr, E is selected from D-Deh and D-Pal(3), F is Leu, G is Deh, and J is Ala-NH₂.

The somastostatin analog compounds of greatest interest, and thus, more preferred, herein are those polypeptide compounds that are the subject of U.S. Ser. No. 233,690 filed Aug. 18, 1988 and owned in common by the assignee of this application. These polypeptides are represented by the formula:

and the pharmaceutically acceptable salts thereof wherein,

X is an N-terminus cationic anchor;

Y is a C-terminus anchor, G-I or alcohol of G-I;

D is Phe, Tyr, pF-Phe, pCl-Phe;

E is Lys or Lys(R₁) where R₁ is a lower alkyl or fluoroalkyl of from 1 to 8 carbon atoms;

F is Thr, Val, Ser;

G is D or L configuration of Thr, Phe, or Nal(2); and

I is —OH or —NHR₂ where R₂ is H or a substituent selected from R₁ above, and wherein an anchor is a biologically acceptable covalently-bound, amino acid moiety that is attached to one of the Cys groups depicted in the formula above and a cationic anchor will have a positively charged function, namely the N^ω alkyl-basic amino acid class, attached to the pharmacophore either directly or through a spacer.

When the cationic anchor is attached to the N-terminus, a Thr-type residue or hydrophobic residue or another cationic anchor may be attached to the C-terminus. When the cationic anchor is attached to the C-terminus, a hydrophobic residue or another cationic anchor may be attached to the N-terminus.

In a yet more preferred embodiment of the somatostin analogs according to the formula given above, X is an N-terminus cationic anchor of the general formula:

A-B$_m$-(C)$_n$ where A is acyl or H;

B is hArg(R₁,R₂), Arg (R₁,R₂) or Lys(R₁), where R₁ is lower alkyl or fluoroalkyl of from 1 to 8 carbon atoms and R₂ is H or a substituent selected from R₁ or other ω-alkyl-basic amino acids;

m is an integer from 1 to 3;

C is a spacer such as Gly, Ala, β-Ala; and n is an integer from 0 to 5.

Compounds that are particularly useful are those where n is 0 or 1.

An alcohol of G-I refers to the alcohol derived from the amino acid moiety which G-I represents. For example, if G-I is Thr-OH, i.e.

the alcohol would be

Most preferred among said somatostatin analogs are compounds represented by the formula:

wherein Z represents a member selected from the group of Deh and Bth wherein Deh represents N',N'-guanidino—(diethyl)-homoarginyl (also abbreviated hArg(Et)₂) and wherein Bth represents N',N'-guanidino-bis(2,2,2-trifluoroethyl)-homoarginyl (also abbreviated hArg (CH₂CF₃)₂.

The polypeptides utilized in the present invention may be synthesized by any techniques that are known to those skilled in the peptide art as are disclosed in the patents and patent applications specifically mentioned. An excellent summary of the many techniques so available may be found in J. M. Stewart and J. D. Young, *Solid Phase Peptide Synthesis* 2nd edit. Pierce Chemical Co., Rockford, Ill., 1984, and J. Meienhofer, *Hormonal Proteins and Peptides*, Vol. 2, p. 46., Academic Press (New York), 1973 for solid phase peptide synthesis and E. Schroder and K. Lubke, *The*

*Peptides,* Vol. 1, Academic Press (New York), 1965 for classical solution synthesis.

In general, these methods involve the sequential addition of one or more amino acids or suitably protected amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the crude, reduced form of the polypeptide. The peptide is oxidatively cyclized in dilute aqueous solution using, for example, air ($O_2$), potassium ferricyanide, $I_2$, $ICH_2CH_2I$, and the like, especially potassium ferricyanide. Finally the peptide is desalted and purified chromatographically to yield the final product.

By "therapeutically effective amount" is meant that amount of the biologically active polypeptide which will elicit the desired therapeutic and/or prophylactic effect (or utility).

The following physiological and paradoxical utilities are known for the LHRH agonist compounds:

Physiological Utilities (Low Dose Effects):
- ovulation induction in anovulatory infertility and for timed ovulation in female mammals;
- therapy for infertility due to insufficient luteal function in women;
- therapy for hypogonadotrophic or hypogonadal infertility in either sex-human.
- Therapy for cystic ovary, nymphomania syndrome in cattle;
- induction or enhancement of sexual behavior or therapy for impotence/frigidity.

Paradoxical Utilities (High Dose Effects):
- female contraception;
- ovulation suppression or delay;
- induction of parturition;
- synchronization of ovulation;
- estrus suppression;
- growth promotionic in female animals;
- luteolysis, menses inductions;
- early, first trimester abortifacient;
- therapy for endometriosis;
- therapy for mammary tumors and cysts;
- therapy for polycystic ovary syndrome (Stein-Leventhal);
- therapy for uterine carcinoma;
- therapy for benign prostatic hypertrophy and for prostatic carcinomas;
- male contraception;
- therapy for diseases which result from excessive gonadal hormone production in either sex;
- functional castration in male food producing animals;
- suppression of proestrous discharge.

In general for the uses of the LHRH agonists described which are so-called "paradoxical" or high-dose uses, it is expedient to administer the active ingredient in amounts between about 0.001 and 10 mg/kg body weight per day, preferably between about 0.001 and 1.0 mg/kg body weight, more preferably between about 0.01 and 0.20 mg/kg body weight per day. This administration may be accomplished by a single daily administration or by distribution over several applications. Ideally, the desired amount of drug is given in a single dose.

The following utilities flow from the LHRH antagonist compounds herein:
- female contraception;
- ovulation prevention or delay;
- pregnancy termination in domestic animals and pets;
- induction of parturition;
- synchronization of ovulation;
- estrus suppression;
- growth promotion in female animals;
- luteolysis, menses induction;
- therapy for premenstrual syndrome;
- therapy for precocious puberty;
- therapy for uterine leiomyoma;
- early, first trimester abortifacient;
- therapy for endometriosis;
- therapy for mammary tumors and cysts
- therapy for polycystic ovary syndrome/disease;
- therapy for uterine carcinoma;
- therapy for benign prostatic hypertrophy and for prostatic carcinoma;
- male contraception;
- therapy for diseases which result from excessive gonadal hormone production in either sex;
- functional castration in male food producing animals;
- suppression of proestrous bloody discharge in dogs;
- diagnostic utilities, such as predisposition to osteoporosis;
- prevention of ovarian hyperstimulation;
- and other uses as set forth in Vickery, B. H., *Endocrine Reviews,* 7:115 (1986), which is fully incorporated by reference herein.

In general for the uses of the LHRH antagonists described above, it is expedient to administer the active ingredient in amounts between about 0.001 and 5 mg/kg body weight. Preferably, for human therapy, the active ingredient will be administered in the range of from about 0.01 to about 1 mg/kg/day; and for animal therapy, the active ingredient will be administered in the range of from about 0.1 to 1 mg/kg/day. This administration may be accomplished by a single administration, by distribution over several applications or by slow release in order to achieve the most effective results. Most preferably, for the interruption of heat or prevention of pregnancy in animals, the dose will be in the range of from about 1 to 10 mg/kg, administered as a single dose.

The use of the somatostatin analogs of the instant invention includes the treatment of somatostatin-regulated human disease states. Among these are applications in "Carcinoid Syndrome", peptic ulcers, ileostomy-caused diarrhea, suppression of endocrine product secretion from "apudomas" and inappropriate secretion of glucagon and growth hormone in diabetes with particular application to the complications of diabetes including retinopathy, nephropathy, hypertension and coronary artery disease.

The somatostatin analogs also may be used to cause tumor regression, especially those tumors expressing epidermal growth factor (EGF) receptors, for example, pituitary adenomas, brain tumors (e.g., meningioma) tumors, abdominal (carcinoid) tumors, endocrine tumors and pancreatic tumors. (See, Lamberts, ISI Atlas of Science: Pharmacology, pp. 179–184 (1988) and references cited therein.

In general for the above uses of the somatostatin analogs it is expedient to administer the active ingredient in amounts between about 0.001 and 1000 μg/kg body weight, preferably from about 0.01 to 100 μg/kg body weight. For human therapy, the active ingredient will be administered more preferably in the range of from about 0.01 to about 50 mg/kg/day. This administration may be accomplished by a single administration, by distribution over several applications or by slow release in order to achieve the most effective results. When administered as a single dose, administration will most preferably be in the range of from about 0.01 to 10 μg/kg.

The exact dose and regimen for administration of these compounds in the compositions according to the present invention will necessarily be dependent upon the needs of the individual subject being treated, the type of treatment, and the degree of affliction or need.

The membrane permeability enhancing agent, which promotes absorption of the polypeptide from the intestinal tract, is preferably a bile acid or alkali metal salt thereof selected from the group of cholic acid, chenodeoxycholic acid, taurocholic acid, taurochenodeoxycholic acid, glycocholic acid, glycochenocholic acid, lithocholic acid, taurolithocholic acid, ursodeoxycholic acid, dehydrochlic acid, deoxycholic acid, glycodeoxycholic acid, taurodeoxycholic acid, 3-beta-monohydroxycholic acid, 3-alpha-hydroxy-12-ketocholic acid, 3-beta-hydroxy-12-ketocholic acid, and 12-alpha-3-beta-dihydrocholic acid.

The bile acid or alkali metal salt thereof preferably is used in an amount of about 0.5–1000 mg/dose, more preferably about 5–500 mg/dose, most preferably about 50–200 mg/dose.

The protease inhibitor used in the composition according to this invention may be any material which has the ability to inhibit any proteolytic activity.

Thus, the protease inhibitor can be/may be selected from the group of aprotinin (Trasylol™), FK-448, chymostatin, leupeptin, N-ethylmaleimide, E-664, elastatinal, pepstatin, FOY-305, bestatin, pentamidine isethionate, antipain, tosylamide-phenethyl-chloromethyl ketone (TPCK), phenylmethyl sulfonylfluoride (PMSF), trypsin inhibitor, acetone, alcohols, guanidium, $\alpha_2$-macroglobulin, TLCK, chelating agents of Zn, iodoacetate, $\alpha_1$-antitrypsin, EDTA, Zn, antithrombin-III, trypsin inhibitor from soy bean, trypsin inhibitor from hen egg white, and trypsin inhibitor from chicken egg white.

Because of its ready commercial availability, the preferred protease inhibitor is aprotinin (Trasylol™ available from Bayer). Trasylol™ contains 10,000 KIU (Kallikrein Inactivator Units) per ml in a sterile isotonic solution, 10 ml. per ampoule (100,000 KIU). One KIU is equivalent to 0.14 μg of the crystalline active ingredient. Thus, the best mode for practicing this invention involves the composition according to this invention wherein the protease inhibitor is aprotinin. Aprotinin is used in the compositions according to this invention preferably in the amount of about 1000–50,000 KIU (0.14–7.0 mg)per dose, most preferrably about 10,000 (1.4 mg) KIU per dose.

The expression, "Kallikrein Inactivator Units" (abbreviated "KIU") is described in Werle, E., Trasylol: A Short Survey on its History, Biochemistry and Activities. New Aspects of Trasylol Therapy, 5, 9–16, Schattauer, Stuttgart-New York, 1972.

The enterocoating material may be selected from any conventional enterocoating material which is known to those skilled in the art to which this invention relates, and which provides protection for the polypeptide against decomposition in the stomach and for release in the gastro-intestinal tract at least up to the point at which the pH required to break-down the enterocoating is reached.

Preferably the enteric coating material will provide for release of polypeptide at about pH 4.0–8.0, more preferably about 5–7.5, most preferably about 5.5–7.0.

Suitable enteric coating materials include the following:
Polyvinyl Derived Polymers:

| Organic Solvent Soluble | | |
|---|---|---|
| PVAP Polyvinyl Acetate Phthalate | | pH 4.8 |
| (Manufacturer: Color Con (USA)) | | |
| Eudragit S Methracrylic Acid Copolymer | | pH 7.0 |
| (Manufacturer: Rohm Pharma, W. Ger.) | | |
| Aqueous Dispersions | | |
| COATERIC Colloidal Dispersion of PVAP | | pH 5.0 |
| (Manufacturer: Color Con (USA) | | |
| Eudragit L Aq. Dispersion of Eudragit | | pH 5.5 |
| (Type B) | | |
| (Manufacturer: Rohm Pharma, W. Ger.) | | |

Cellulose Derived Polymers:

Organic Solvent Soluble

| HPMCP | Hydroxypropylmethyl/cellulose Phthalate | pH 5 (HP-50) pH 5.5 (HP-55) |
|---|---|---|
| (Manufacturer: Shin Etsu (Japan) | | |
| HPMC-AS | Hydroxypropylmethylcellulose Acetate | pH 5.0 pH 5.5 pH 6.0 |
| (Manufacturer: Shin Etsu (Japan) | | |
| CAP | Cellulose Acetate Phthalate Succinate | pH 6.3 |
| (Manufacturer: Eastman Kodak (USA) | | |
| CAT = Cellulose Acetate Trimellitate | | pH 5.5 |
| (Manufacturer: Eastman Kodak (USA) | | |
| Aqueous Dispersions | | |
| HP-55-AF | Aq. Colloidal Dispersion of HPMCP-5 5 | Ph 5.5 |
| (Manufacturer: Shin Etsu (Japan)) | | |
| AQOAT | Aq. Colloidal Dispersion of HPMC-AS | pH (Same as HPMC-AS above) |
| (Manufacturer: Shin Etsu (Japan)) | | |
| AQUATERIC | Aq. Colloidal Dispersion of CAP | pH (Same as CAP above) |
| (Manufacturer: FMC Inc (USA) | | |

Preferably, for the purposes of illustrating this invention in the monkey, the enteric coating material is selected from HPMC-AS (pH 5.5), CAT (pH 5.5) and Eudragit L (pH 5.5), most preferrably Eudragit L (pH 5.5).

Preferably, for use in the human, we believe the enteric coating material preferably should be one which will provide for release of polypeptide at about pH 6.0–6.5 such as, for example, CAP and HPMC-AS.

The enterocoating is carried out by methods known per se in the art, e.g., according to Remington Pharmaceutical Sciences, p. 1614–1615 (1975, 15th Ed., Mack Pub. Co.) and Theory and Practice of Industrial Pharmacy, Lackman, Liberman & Caning, p. 116-117, 371–374 (1976, 2nd Ed.). The enteric micro-encapsulation process is also known. (Theory and Practice of Industrial Pharmacy ibid, pp. 420–438). See also Remington Pharmaceutical Sciences, p. 1637 (1985, 17th Ed., Mack Pub. Co.). Typically, the amount of enteric coating material used preferably is in the range about 10–20 mg per 500 $cm^2$ of surface area of capsule or tablet, especially of capsule as produced in the actual examples described herein below. The amount of enteric coating material broadly is in the range of about 1–5000 mg/capsule, more preferably about 10–1000 mg/capsule, most preferably about 50–100 mg/capsule.

The composition according to this invention comprising the biologically active polypeptide, bile acid or salt thereof, protease inhibitor, and enteric coating material together with a pharmaceutically acceptable carrier (or excipient) can be formulated for oral administration in the form of a liquid, for example solutions or suspensions or emulsions; a tablet; a capsule; or a lozenge. For purposes of this invention, the expression "carrier" (and "excipient") mean any vehicle conventionally used in the delivery of pharmaceuticals agents including diluents or fillers and sterile aqueous media or non-toxic organic solvents and also conventional adjuvants.

A liquid formulation will generally consist of a solution or suspension containing the biologically active polypeptide and bile acid salt and protease inhibitor filled into a pharmaceutically acceptable capsule for example, a standard or conventional hard gelatin capsule and the filled capsule will be coated. The solution or suspension which is filled into such capsule will generally consist of the biologically active polypeptide and bile acid or bile acid salt and protease inhibitor dissolved or suspended in any pharmaceutically acceptable liquid carrier such as, for example, a sterile aqueous carrier or water-miscible solvents such as, for example, ethanol, glycerin, propylene gylcol and sorbitol, or mixtures of any of the foregoing.

A tablet formulation can be prepared by admixing the biologically active polypeptide and bile acid or bile acid salt and protease inhibitor with any conventional pharmaceutically acceptable, compatible carrier (or excipient) and other adjuvants. For example, carriers (or excipients) such as lactose, starch, sucrose and binders such as film forming polymers such as cellulose acetate phthalate and hydroxypropylmethyl cellulose phthalate amd vinyl polymers such as methyl methacrylate-methacrylic acid copolymers and disintegrants such as starch and alginic acid and certain complex silicates and lubricants such as magnesium stearate, sodium lauryl sulfate and talc can be used in producing tablets. The admixture of polypeptide, bile acid or salt thereof, protease inhibitor and carrier and other optional adjuvants can be compressed into tablets which are then enterocoated employing techniques conventional in the art.

Preferably, the composition according to this invention is in unit dose form containing the daily therapeutically effective dose of polypeptide for a patient having a body weight of about 45–100 kg and the amounts of bile acid or bile salt and protease inhibitor and enteric coating material set forth above. The amounts of carrier (or excipient) and enteric coating material and the choice of particular carrier and the ratio of active polypeptide and other required ingredients (namely, bile acid or salt thereof, protease inhibitor and enteric coating material) to carrier can vary and are not deemed to be critical.

Generally, depending upon the selection of the biologically active polypeptide, the unit dosage form of the composition according to this invention will contain the following:

(a) from about 0.000045 mg to about 1,000 mg of biologically active polypeptide;

(b) from about 0.5 mg to about 1000 mg of bile acid or alkali metal salt thereof;

(c) from about 0.14 mg to about 7.0 mg of aprotinin; and (d) from about 1 to about 5000 mg of enteric coating material.

Referring to the formulations given in Table I for administration in capsule form, compositions having Formulations A, B, and C were produced by the following steps:

Preparation on Lab Scale a. Mix propylene glycol and sorbitol.

b. Dissolve peptide (Formulation A) or peptide plus glycocholate (Formulation B) or peptide plus glycocholate plus aprotinin (Formulation C) in (a).

c. Measure (b) into hard gelatin capsules.

d. Seal capsules (c) with liquified gelation.

e. Immerse capsules (d) in Eudragit L-100 to give 12.5% w/v of polymer solubilized with sufficient acetone to afford solution and triethyl citrate in an amount sufficient to give 1.25% w/v.

f. Air dry coated capsules (e).

All reagents which were used in producing the compositions having Formulations A, B, and C were bulk materials of USP grade.

For preparation of capsules according to this invention on larger clinical size scale, steps (a) and (b) would be carried-out in large scale mixing equipment that is standard in the art. Capsule filling and sealing would be carried out in a conventional capsule filling and capsule banding apparatus. Enteric coating and drying the coated capsules would be carried out in conventional enterocoating apparatus.

The following examples, including table and figures herein described, are illustrative of the invention and are not be be construed as limiting in scope.

EXAMPLES

Comparison Composition A

Preparation of Capsules Containing Formulation A 2.5 g of propylene glycol (USP) and 2.5 g of sorbitol (USP, 70% in aqueous solution) were admixed by hand in a 50 ml beaker. Then, 46 mg of RS-94991-268 (nafarelin acetate, Syntex) was admixed by hand with the mixture from above. The amounts of each ingredient were selected such that ten portions and ten capsules could be produced per batch. The propylene glycol-sorbitol-nafarelin acetate mixture was measured using a pipette in 0.5 ml portions into hard gelatin capsules (size #0 blue opaque capsules supplied by ELANCO) so as to provide seven capsules containing 4.6 mg of nafarelin acetate and 250 mg of sorbitol and 250 mg of propylene glycol per capsule. The filled capsules were then sealed using liquified gelatin. (ELANCO Gelatin was heated to melting temperature and sufficient quantity to seal each capsule was applied by hand-brush). Next, the sealed capsules were immersed (each capsule was tethered by thread using a drop of liquified gelatin) in a solution of 5 g of Eudragit L-100-55 (an aqueous dispersion of a methacrylic acid methylmethacrylate copolymer, pH 5.5, available from Rohm Pharma) (12.5% w/v) dissolved in 0.5 g of triethyl citrate (1.25% w/v) and acetone q.s. to 40 ml. Finally, after removal from the enterocoating material—Eudragit L polymer—solution bath, the capsules were suspended by the thread and air dried for 1 hour. The thread was pulled loose from each capsule and the thread-tip end of the capsule was hand-dipped into the Eudragit L-100-55 solution and air-dried as above.

Comparison Composition B

Preparation of Capsules Containing Formulation B

Capsules containing Formulation B were produced by following substatioally the procedure set forth in the Preparation of Capsules Containing Formulation A above except that 1 g of sodium glycocholate was combined with the 46 mg of RS-94991-268 (nafarelin acetate) and this combination added to the mixture of propylene glycol and sorbitol. Capsules were filled and then coated as in the Preparation of Capsules Containing Formulation A procedure.

Example 1

According to this Invention

Preparation of Capsules Containing Formulation C

Capsules containing Formulation C were produced by following substantially the procedure set forth in the Preparation of Capsules Containing Formulation A except that 1 g of sodium glycocholate along with 14 mg of aprotinin (a protease inhibiting enzyme available under the trademark, Trasylol-TM, from Bayer) (10,000 K.I.U.) was combined with the 46 mg of RS-94991-268 (nafarelin acetate) and this combination was added to the mixture of propylene glycol and sorbitol. Capsules were filled and then coated as in the procedure referred to hereinabove.

Capsules containing composition according to this invention wherein the biologically active polypeptide is an LHRH antagonist or a somatostatin analog can be produced by following substantially the procedure set forth in Example 1 except for substituting the desired amount of LHRH antagonist or somatostatin analog for the LHRH angonist nafarelin acetate.

Biological Testing

The so-produced capsules containing the compositions of Formulas A, B, and C were tested for oral absorption in monkeys as described below.

Table I summarizes the composition of two comparison formulations representative of the prior art, namely, Formulations A and B; Formulation C illustrates a typical composition according to the present invention wherein the biologically active polypeptide designated RS-94991-298 is nafarelin acetate, an LHRH agonist.

The compositions were enteric coated according to procedures described hereinabove.

In our studies, Rhesus monkeys were orally administered single 5 mg doses of one of the three different capsule formulations. Three monkeys were tested on each of Formulations A, B and C. Each monkey was dosed once in a 3-way cross-over design test with a 1-week "washout" period between each dose. Plasma concentration of nafarelin acetate was determined 24 hours after treatment. The plasma concentration of nafarelin acetate was determined using the radio-immunoassay (RIA) method of C. Nerenberg, et al., *Analytical Chem.*, 144, 10–16(1984).

All formulations contained RS-94991-298 (nafarelin acetate) solubilized in sorbitol and propylene glycol and were enteric coated (Comparison Formulation A). In addition to the foregoing contents of, Formulation A, Comparison Formulation B contained 100 mg of sodium glycolate. In addition to the foregoing contents of Formulation B, Formulation C according to this invention, contained both 100 mg of sodium glycocolate and 10,000 KIU of aprotinin.

Figure 1:
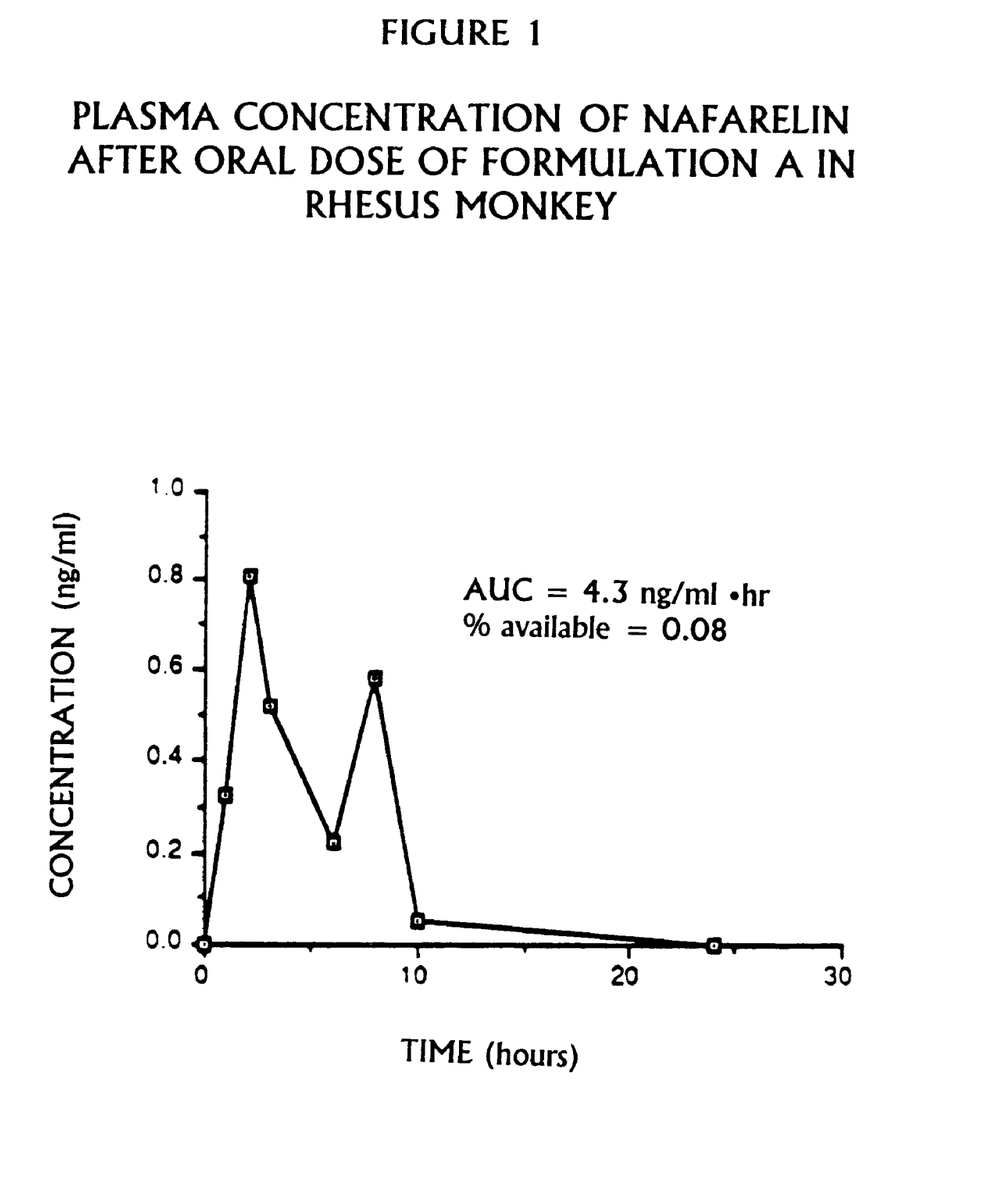
FIG. 1 shows the plasma concentration of nafarelin acetate after oral dosage of a composition known in the art having Formulation A in Rhesus monkey.
Figure 2:
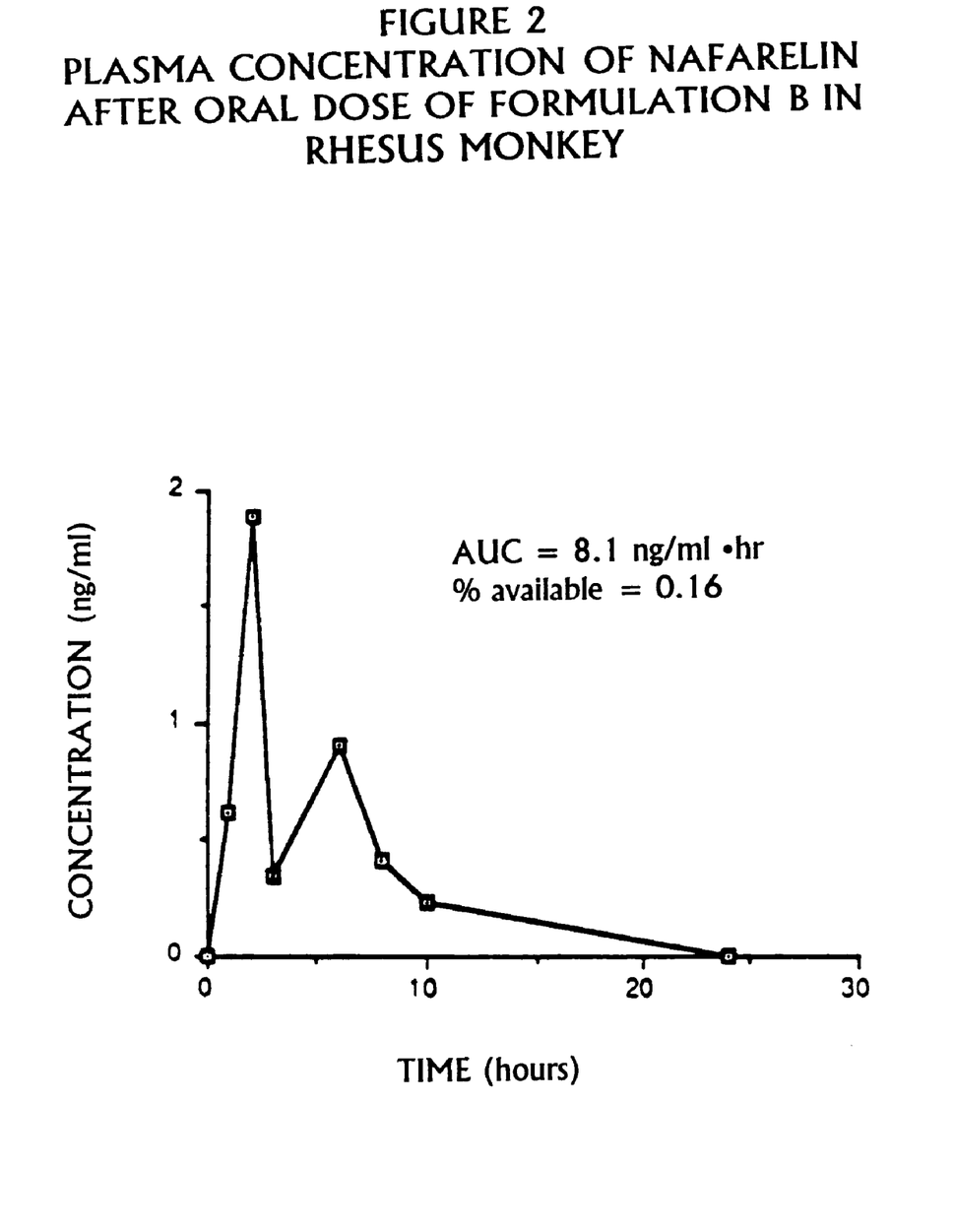
FIG. 2 shows the plasma concentration of nafarelin acetate after oral dosage of a composition known in the art Formulation B in Rhesus monkey.
Figure 3:
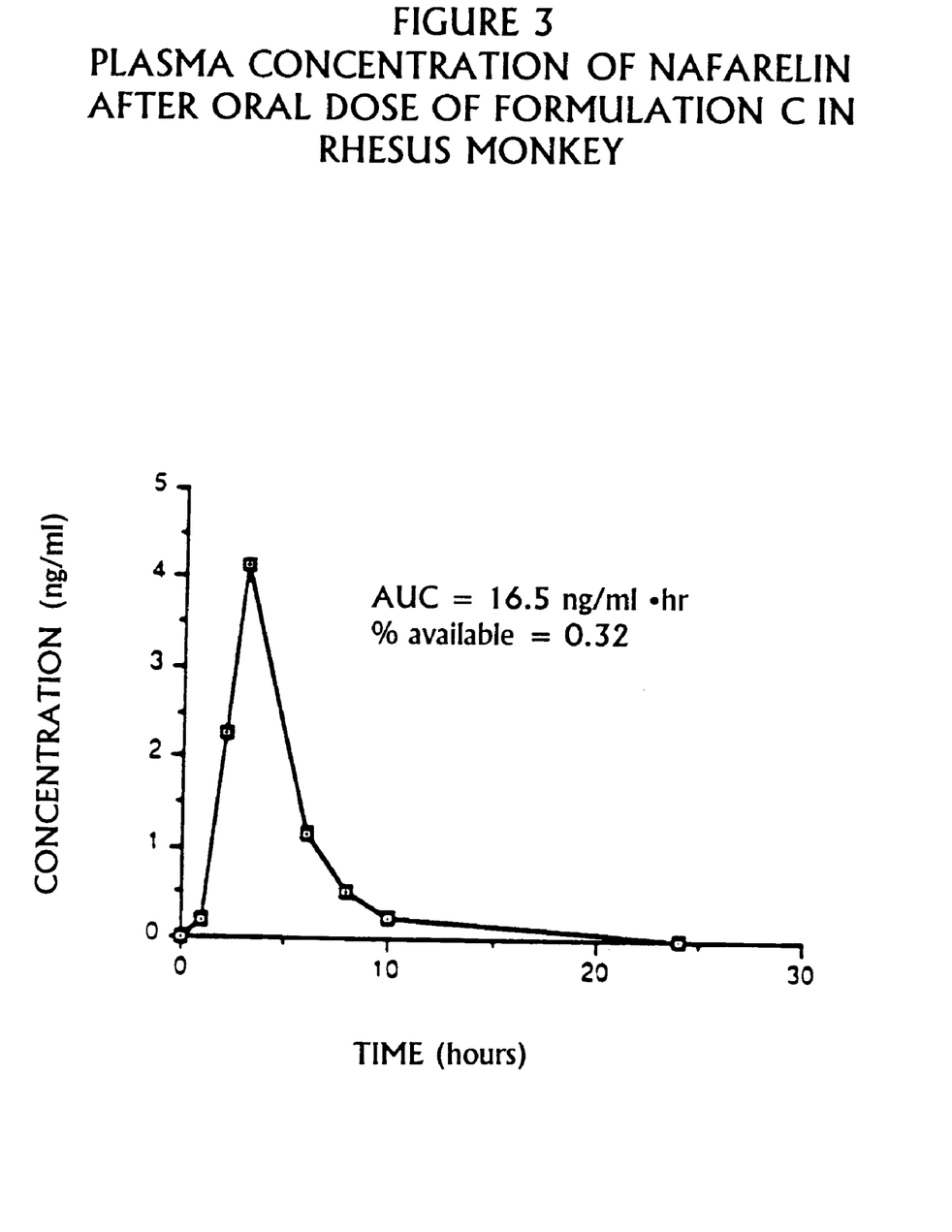
FIG. 3 shows the plasma concentration of nafarelin acetate after oral dosage of Formulation C in Rhesus monkey, Formula C being representative of a composition according to this invention.

The results (FIGS. 1, 2 and 3) demonstrated that for the enteric coated formulation of active ingredient, nafarelin acetate, alone (Formulation A), intact nafarelin was absorbed, although the bioavailability was quite low (0.08%). Plasma levels well over the accepted therapeutic level of 0.1 ng/ml were achieved for at least 8 hours. Formulation B containing the bile, salt demonstrated double the biovailability obtained from Formulation A, and the addition of aprotinin (Formulation C) gave four times the bioavailability obtained from enteric coating alone.

Figure 4:
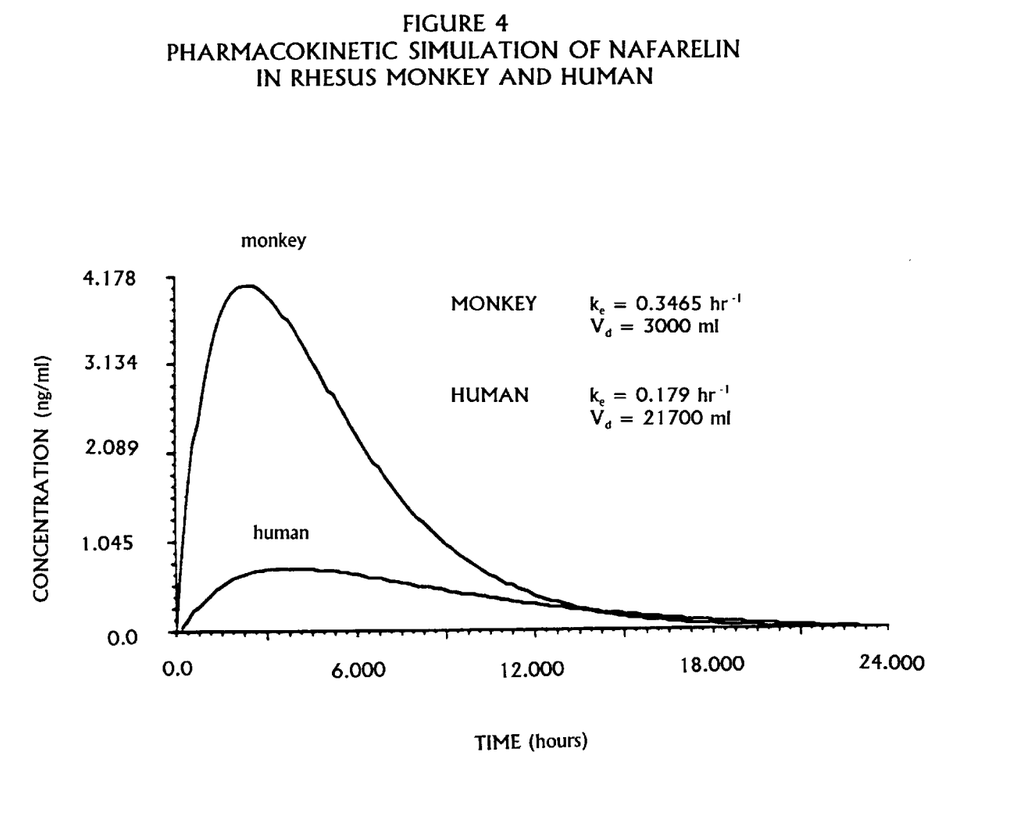
FIG. 4 shows the pharmacokinetic simulation of nafarelin acetate in Rhesus monkey and man using the composition of Formula C according to this invention.

Pharmacokinetic simulations of the data obtained have been extrapolated to humans, using the results from Formulation C and an equivalent dose. See FIG. 4. From this we predict that single 5 mg doses provide therapeutic levels of nafarelin for greater than 12 hours using some type of site directed delivery, for example, enteric coating, in conjunction with these adjuvants (namely, bile salts and protease inhibitors).

What is claimed is:

1. A pharmaceutical composition suitable for oral administration to a human patient comprising:
   (a) a therapeutically effective amount of a biologically active peptide selected from the group consisting of an LHRH analog and a somatostatin analog;
   (b) a membrane permeability enhancing agent selected from a bile acid or an alkali metal salt thereof;
   (c) a non-toxic amount of a protease inhibitor; and
   (d) an enteric coating material, said enteric coating material enveloping the admixture of components (a), (b), and (c).

2. A composition according to claim 1 wherein said biologically active polypeptide is an LHRH analog.

3. A composition according to claim 2 wherein said LHRH analog is selected from LHRH agonists and LHRH antagonists.

4. A composition according to claim 3 wherein said LHRH analog is an LHRH agonist.

5. A composition according to claim 4 wherein said LHRH agonist is a polypeptide represented by the formula:

(pyro)Glu.His.Trp.Ser.Tyr.3-(2-naphthyl)-D-Ala.Leu.Arg.Pro.Gly-NH$_2$.

6. A composition according to claim 3 wherein said LHRH analog is an LHRH antagonist.

7. A composition according to claim 6 wherein said LHRH antagonist is a polypeptide represented by one of the formulas:

N-Ac-D-Nal(2).D-pCl-Phe.D-Pal(3).Ser.Tyr.D-Pal(3).Leu.Deh.Pro.Ala-NH$_2$ and

N-Ac-D-Nal(2).D-pCl-Phe.D-Pal(3).Ser.Tyr.D-Deh.Leu.Deh.Pro.Ala-NH$_2$.

8. A composition according to claim 1 wherein said biologically active polypeptide is selected from a somatostatin analog.

9. A composition according to claim 8 wherein said somatostatin analog is selected from compounds represented by the formula:

wherein Z represents a member selected from the group of Deh and Bth wherein Deh represents N',N'-guanidino-(diethyl)-homoarginyl (also abbreviated hArg(Et)$_2$) and wherein Bth represents N',N'-guanidino-bis-(2,2,2-trifluoroethyl)-homoarginyl (also abbreviated hArg (CH$_2$CF$_3$)$_2$.

10. A composition according to claim 1 wherein said membrane permeability enhancing agent is a bile acid or alkali metal salt thereof selected from the group of cholic acid, chenodeoxycholic acid, taurocholic acid, taurochenodeoxycholic acid, glycocholic acid, glycochenocholic acid, lithocholic acid, taurolithocholic acid, ursodeoxycholic acid, dehydrochlic acid, deoxycholic acid, glycodeoxycholic acid, taurodeoxycholic acid, 3-beta-monohydroxycholic acid, 3-alpha-hydroxy-12-ketocholic acid, 3-beta-hydroxy-12-ketocholic acid, and 12-alpha-3-beta-dihydrocholic acid.

11. A composition according to claim 1 wherein said protease inhibitor is selected from the group of aprotinin (Trasylol™), FK-448, chymostatin, leupeptin, N-ethylmaleimide, E-664, elastatinal, pepstatin, F0Y-305, bestatin, pentamidine isethionate, antipain, tosylamide-phenethyl-chloromethyl ketone(TPCK), phenylmethyl sulfonylfluoride (PMSF), trypsin inhibitor, acetone, alcohols, guanidium, a$_2$-macroglobulin, TLCK, chlating agents of Zn, iodoacetate, a$_1$-antitrypsin, EDTA, Zn, antithrombin-III, trypsin inhibitor from soy bean, trypsin inhibitor from hen egg white, and trypsin inhibitor from chicken egg white.

12. A composition according to claim 1 wherein said enteric coating material is selected from the group consisting of organic solvent soluble polymers and dispersions of polymers, said polymers having a pH of about 5–7.5 and said polymers being selected from the group comprising polyvinyl acetate pthalate, methacrylic acid copolymers, hydroxypropylmethylcellulose phthalate, hydroxypropylmethylcellulose acetate succinate, cellulose acetate phthalate, and cellulose acetate trimellitate.

13. A composition according to claim 1 wherein the mount of biologically active polypeptide (a) is about 0.000045 mg to about 1,000 mg, the amount of bile acid or alkali metal salt thereof (b) is about 0.05 mg to about 1000 mg, the amount of aprotinin as the protease inhibitor (c) is about 0.14 mg to about 7.0 mg, and the amount of enteric coating material (d) is about 1 mg to about 500 mg.

14. A pharmaceutical composition suitable for oral administration to human patient in the form of a gelatin capsule comprising:
   (a) about 0.045 mg/kg to about 1,000 of the LHRH agonist, nafarelin acetate;
   (b) about 50 mg to 200 mg of the membrane permeability enhancing agent, sodium glycochlolate acid;
   (c) about 1.4 mg (10,000 KIU) of the protease inhibitor, aprotinin; and
   (d) about 50 mg to about 100 mg of the methacrylic acid copolymer enteric coating material Eudragit L, said enteric coating material enveloping the capsule containing the admixture of components (a), (b) and (c).

15. A process for providing a pharmaceutical composition suitable for oral administration comprising the steps of (1) admixing
   (a) a therapeutically effective amount of biologically active polypeptide selected from an LHRH analog and a somatostatin analog,
   (b) a membrane permeability enhancing agent selected from a bile acid or an alkali metal salt thereof, and
   (c) a non-toxic amount of a protease inhibitor, and (2) coating the resulting mixture with an enteric coating material said composition being provided in a pharmaceutically acceptable dosage form selected from capsule and tablet forms.

16. A method of administering a therapeutically effective amount of a biologically active polypeptide selected from an LHRH analog and a somatostatin analog, comprising orally administering the composition of claim 1.

* * * * *